United States Patent [19]

Polak et al.

[11] Patent Number: 4,560,444
[45] Date of Patent: * Dec. 24, 1985

[54] GAS DETECTION WITH NOVEL ELECTROLYTE MEMBRANE AND SOLID INTERNAL REFERENCE

[75] Inventors: Anthony J. Polak, Lake Zurich; Allyson J. Beuhler, Indian Head Park, both of Ill.

[73] Assignee: UOP Inc., Des Plaines, Ill.

[*] Notice: The portion of the term of this patent subsequent to Feb. 19, 2002 has been disclaimed.

[21] Appl. No.: 566,845

[22] Filed: Dec. 29, 1983

[51] Int. Cl.$^4$ ............................................. G01N 27/58
[52] U.S. Cl. ..................................... 204/1 T; 204/421; 204/426; 204/427
[58] Field of Search ................. 204/421, 424, 426, 1 T, 204/1 B, 1 F, 1 S, 427; 429/33, 192

[56] References Cited

U.S. PATENT DOCUMENTS

| | | | |
|---|---|---|---|
| 3,265,536 | 8/1966 | Miller et al. | 136/86 |
| 3,276,910 | 10/1966 | Grasselli et al. | 136/86 |
| 3,379,571 | 4/1968 | Piret | 429/33 |
| 3,410,780 | 11/1968 | Holden | 204/426 X |
| 3,727,058 | 4/1973 | Schrey | 204/424 X |
| 4,024,036 | 5/1977 | Nakamura et al. | 204/129 |
| 4,040,929 | 8/1977 | Bauer et al. | 204/195 S |
| 4,179,491 | 12/1979 | Howe et al. | 423/253 |
| 4,306,774 | 12/1981 | Nicholson | 350/357 |
| 4,324,760 | 4/1982 | Harris | 422/98 |
| 4,324,761 | 4/1982 | Harris | 422/98 |
| 4,373,375 | 2/1983 | Terhune et al. | 73/19 |

OTHER PUBLICATIONS

Solid State Ionics 7 (1982), North-Holland Publishing Company, pp. 53–56, "A Novel Hydrogen Gas Sensor Based on Hydrogen Uranyl Phosphate", Lundsgaard et al.

Platinum Metals Review, Jan. 1983, vol. 27, No. 1, p. 8, "Hydrogen Detector uses Silver–Palladium Probe".

Instrumentation Technology, Aug. 1972, pp. 29–31, "A Thin–Film Hydrogen Sensor" by J. R. MacIntyre et al.

*Primary Examiner*—G. L. Kaplan
*Attorney, Agent, or Firm*—Thomas K. McBride; William H. Page, II; Richard J. Cordovano

[57] ABSTRACT

Apparatus and method for detecting and measuring hydrogen and compounds capable of dissociating into or combining with hydrogen ions using a solid electrolyte concentration cell. A solid reference substance is used in place of a reference gas. A novel solid electrolyte membrane is used which comprises an organic polymer-inorganic compound blend prepared by admixing an organic polymer such as poly(vinyl alcohol) with a heteropoly acid or salt thereof such as dodecamolybdophosphoric acid or uranyl orthophosphate in a mutually miscible solvent.

19 Claims, 4 Drawing Figures

GAS DETECTION WITH NOVEL ELECTROLYTE MEMBRANE AND SOLID INTERNAL REFERENCE

BACKGROUND OF THE INVENTION

This invention relates to electrochemical measurement and detection. More specifically, it relates to an improvement in the use of a solid electrolyte and a catalyst in detecting the presence of hydrogen or gases capable of dissociating to yield or combining with hydrogen ions, including oxygen, and measuring the quantity present. The improvement involves the use of a substance in solid form in place of a reference substance in gaseous form.

The use of solid electrolyte sensors for detecting oxygen, particularly in automotive exhaust gases, is well known. The present invention utilizes similar basic principles for detection of certain gases. The Nernst equation describes the behavior of sensing devices using solid electrolytes. When two media with different partial pressures, $P_1$ and $P_2$, of a particular substance present in both media are separated by a solid electrolyte (ionic conductor) and conducting electrodes are attached to both sides of the ionic conductor, an EMF is generated which is related to the partial pressures as follows:

$$EMF = E_o + \frac{RT}{nF} \ln \frac{P_2}{P_1},$$

where R is the gas constant, T is absolute temperature, F is the Farady constant, $E_o$ is the standard oxidation-reduction potential difference, EMF is electromotive force, and n is the number of electrons per molecule of product from the overall cell reaction. If the system described by the above equation behaves non-ideally, the partial pressures must be replaced by fugacities. Another factor which may need to be considered in regard to a particular system is the rate of dissociation to form the ions which pass through the solid electrolyte. This may be a limiting factor to the transfer of ions through the electrolyte. The rate of dissociation can be calculated by means of the equilibrium constant for the dissociation reaction.

A novel solid electrolyte membrane is used in the present invention. We have discovered that a polymer blended membrane may be fabricated by admixing a heteropoly acid or a salt thereof with an organic polymer which is at least partially compatible with said heteropoly acid or salt to form a polymer blended composition of matter which is useful in gas detection. It was totally unexpected that a thin film membrane could be cast from such a blend to provide a membrane which would be highly selective to certain gases and therefore able to act as a proton conductor in a hydrogen detector where molecular hydrogen is converted into protons on one side of the device, transported through the membrane, and recombined as molecular hydrogen on the other side. The membrane is also useful in detecting gases capable of dissociating into or combining with hydrogen ions. Also used in the invention is a solid substance which is a substitute for a reference gas, which reference gas is one of the two media mentioned above in the discussion of the Nernst equation. It is highly desirable to use a solid reference substance, which requires only periodic replacement, instead of maintaining a continuous reference gas flow, or in appropriate situations, maintaining a sealed chamber of reference gas. For background information relating to the present invention, reference may be made to the book *Solid Electrolytes and Their Applications*, edited by Subbarao, Plenum Press, 1980.

BRIEF SUMMARY OF THE INVENTION

It is among the objects of the present invention to provide methods and apparatus of detecting hydrogen ion and therefore dissociable hydrogen compounds and of detecting compounds capable of combining with hydrogen ion in order to indicate the presence or absence of these substances and, where desired, provide quantitative information on the amount present.

The invention utilizes a concentration cell whose electrolyte is a thin film organic-inorganic membrane which conducts hydrogen ions. The membrane is mounted in a sample cell or membrane housing having a sample gas chamber and a reference chamber. The sample gas chamber contains the gas sample of interest, which must include a component capable of dissociating to form hydrogen ions or capable of combining with hydrogen ions. In the other chamber is a reference substance which exhibits a substantially constant known hydrogen partial pressure during use of the invention. The membrane must be substantially imporous so that the gas will not diffuse through it. A catalytic agent for promotion of dissociation or combination is in intimate contact with the membrane on the sample gas side. Catalytic agent is also provided in a like manner on the other side. The reference substance is in intimate contact with the catalytic agent on the reference side of the membrane. It is not necessary that the same catalytic agent be used on both sides. Means for forming electrical contact and transferring electrons to and from an external circuit are provided on each side of the electrolyte in intimate contact with catalytic agent. The cell EMF is measured across said means and provides an indication of the presence of hydrogen or gases capable of combining with it in the sample gas and/or a quantitative measure of the amount of such which is present. The magnitude of EMF produced is generally in accordance with the parameters discussed above: the Nernst equation and, where applicable, the dissociation equilibrium constant. However, required practice in measuring concentration is to periodically calibrate the measuring apparatus by use of samples whose composition is known. Thus, exact adherence to theoretical relationships is not required of commercially used methods and apparatus. The primary commercial requirement is repeatability.

The method of the invention may be summarized as a method for detection, in a gas sample, of a gaseous component which is capable, in the presence of a catalytic agent, of dissociating to yield hydrogen ions or of combining with hydrogen ions, such method comprising contacting said gas sample with a first surface of a thin film organic-inorganic membrane and detecting EMF between means for forming electrical connection with two separate portions of a catalytic agent effective to promote dissociation and combination, where a first portion of catalytic agent is in contact with said first surface and a second portion of catalytic agent is in contact with a second surface of said membrane, which membrane isolates said gas sample from a reference substance which exhibits a substantially constant known hydrogen partial pressure during practice of said method for detection, where the reference substance is in contact with said second catalytic agent portion, and which membrane has said second surface exposed to the reference substance, said membrane comprising a blend of a compound selected from the group consisting of heteropoly acids and salts thereof and a polymer which is at least partially compatible with said compound.

A calculating device may be used to automatically calculate concentrations, or calculation may be accomplished manually. This device may receive input from a temperature probe, or temperature may be entered manually for use in the calculation. Temperature of the gas and/or the membrane housing may be controlled at a preestablished value. The reference substance may be a metal hydride, an example of which is palladium hydride. The catalytic agent may be nickel, platinum, palladium, or alloys thereof. The catalytic agent may be electrically conductive. A single substance may serve as both catalytic agent and reference substance. The form of the electrolyte element may require that sample gas which contacts it be dry or contain water vapor. Where temperature of the sample gas is too high or low for effective detection, it may be adjusted before the gas is contacted with the electrolyte element. It may be necessary to adjust the concentration, in a known manner, of sample gas contacting the membrane in order to achieve effective detection.

DETAILED DESCRIPTION OF THE INVENTION

Figure 1:
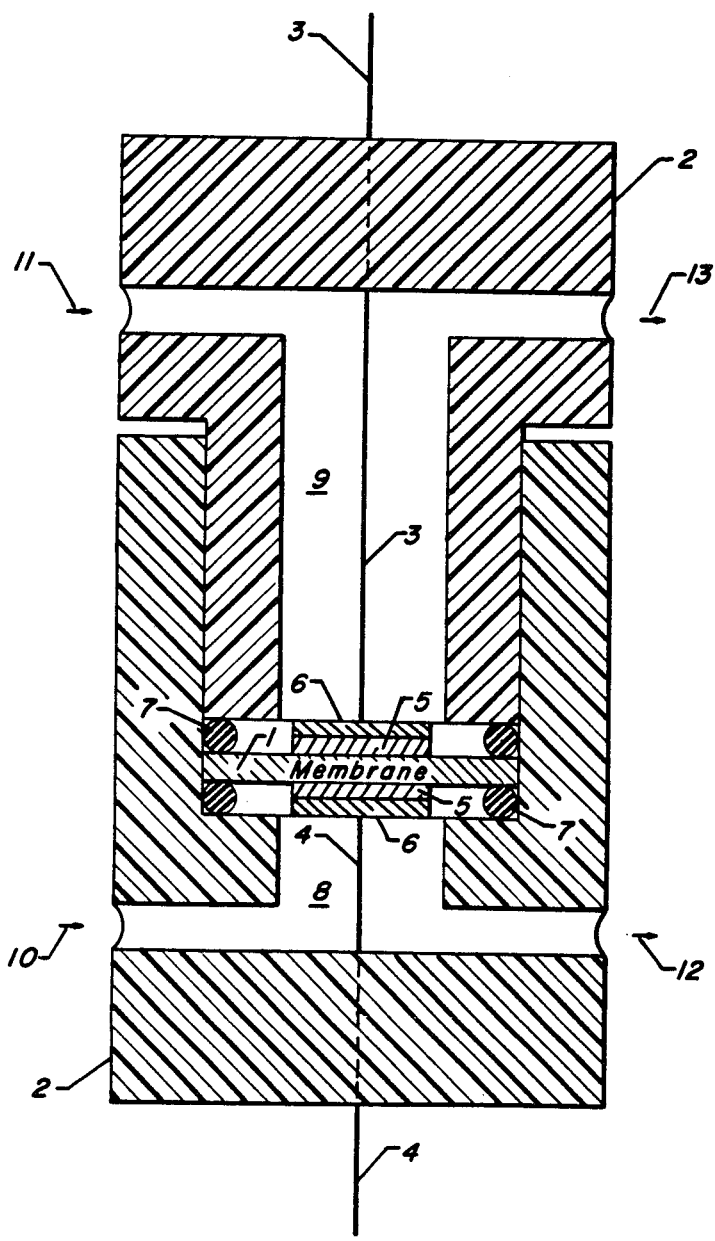
FIG. 1 is a schematic representation, in cross-section, of a test sensor used in initial experimentation, where a reference gas was used instead of a solid reference substance. The drawing is not to scale.

Before the development of the above-mentioned blended membrane, it was attempted to use a heteropoly acid, dodecamolybdophosphoric acid (DMPA) as a solid electrolyte in a gas detector and other similar applications. DMPA purchased in powder form from Alpha-Ventron was pressed at approximately 20,000 psi for about 20 seconds to form a wafer 1 inch in diameter and approximately 3 mm thick. It was necessary to use glass epoxy platens to prevent the DMPA from contacting the steel press dies in order to prevent formation of a blue liquid. Sputter deposition of platinum on the wafer to serve as catalyst was unsuccessful, first because a vacuum suitable for sputter deposition could not be obtained, apparently as a result of the water of hydration in the wafer, and then because the wafer developed cracks which made it unable to function as a gas impermeable barrier. A platinum-impregnated carbonaceous material was successfully fabricated as catalyst and electrode by placing it in the press dies and pressing it along with the DMPA. Impregnation was accomplished by adding chloroplatinic acid to carbonaceous material and decomposing to leave elemental platinum. However, use of this wafer in a gas detector (etc.) suffered from a number of drawbacks, including brittleness of the wafer and difficulty in making good electrical contact between the electrodes and DMPA. Another serious problem was that the amount of water vapor in the gas contacting the wafer had to be maintained in a narrow range to prevent deterioration of the wafer. With too much water, the wafer became spongy and with too little, it cracked. Attention was then directed toward other substances and a novel substance useful in gas detection and similar applications was discovered.

When attempting to blend an organic polymer with an inorganic compound, the usual result is to obtain a phase separation. In contradistinction to this, we have discovered that a single phase system may be obtained by admixing certain organic polymeric compounds with a heteropoly acid or salt thereof, the resulting composition of matter forming a thin film membrane which may be utilized in gas detection systems. The use of these membranes in gas detection devices (etc.) is due in some respect to the fact that heteropoly acids or salts thereof possess a high protonic conductivity, especially at room or ambient temperature. The membranes which are formed from the blend of the organic polymer and the heteropoly acid or salt thereof possess excellent transport properties as well as an increase in tensile strength over those membranes prepared from pure organic polymers. The physical properties which these thin film membranes exhibit thus provide an attractive base for their use as gas sensors (etc.). As will hereinafter be shown in greater detail, the organic-inorganic blends possess chemical, mechanical and electrical properties which indicate the two materials form a single phase system. For example, the blends possess only one glass transition temperature, which indicates a single phase system inasmuch as, if the resulting membranes were a two-phase system, or merely a physical mixture, the composition would possess two separate and distinct glass transition temperatures. In addition, the yield strength and modulus is greatly increased over those properties which are possessed by either of the two components. Another physical characteristic which indicates a single phase or true composition of matter is that the blend is transparent to visible light as well as being uniform in color.

The desired membrane comprises a blend of an organic polymer and a heteropoly acid or salt thereof, the polymer being at least partially compatible with the acid or salt. Examples of organic polymers which may be employed as one component of the blend of the present invention include poly(vinyl alcohol) (PVA), poly(vinyl fluoride), polyethylene oxide, polyethyleneimine, polyacrylic acid, polyethylene glycol, cellulose acetate, polyvinylmethylethyl ether, phenol formaldehyde resins, etc.

Examples of heteropoly acids or salts thereof which may be employed as the second component of the organic-inorganic blend which may be used to form a membrane will possess the generic formula:

$$A_m[X_x Y_y O_z] \cdot n\, H_2O$$

in which X and Y may be selected from the group consisting of boron, aluminum, gallium, silicon, germanium, tin, phosphorus, arsenic, antimony, bismuth, selenium, tellurium, iodine, and the first, second, third and fourth transitional metal series, said series including scandium, yttrium, lanthanum, actinium, titanium, zirconium, hafnium, vanadium, niobium, tantalum, chromium, molybdenum and tungsten, X and Y being dissimilar in nature, A is selected from the group consisting of hydrogen, ammonium, sodium, potassium, lithium, rubidium, cesium, beryllium, magnesium, calcium, strontium and barium, m is an integer of from 1 to 10, y is an integer of from 6 to 12 based on x taken as 1, z is an integer of from 30 to 80 and n is an integer of from 3 to 100.

Specific examples of these compounds will include dodecamolybdophosphoric acid (DMPA), ammonium molybdophosphate, sodium molybdophosphate, potassium molybdophosphate, lithium molybdophosphate, calcium molybdophosphate, magnesium molybdophosphate, dodecatunstophosphoric acid, ammonium tungstophosphate, sodium tungstophosphate, potassium tungstophosphate, lithium tungstophosphate, calcium tungstophosphate, magnesium tungstophosphate, dodecamolybdosilicic acid, ammonium molybdosilicate, sodium molybdosilicate, potassium molybdosilicate, lithium molybdosilicate calcium molybdosilicate, magnesium molybdosilicate, dodecamolybdogermanic acid, ammonium molybdogermanate, sodium molybdogermanate, potassium molybdogermanate, lithium molybdogermanate, calcium molybdogermanate, magnesium molybdogermanate, hexamolybdotelluric acid, ammonium molybdotellurate, sodium molybdotellurate, potassium molybdotellurate, lithium molybdotellurate, calcium molybdotellurate, magnesium molybdotellurate, dodecatungstosilicic acid, ammonium tungstosilicate, sodium tungstosilicate, potassium tungstosilicate, lithium tungstosilicate, calcium tungstosilicate, magnesium tungstosilicate, etc. It is also contemplated within the scope of this invention that some uranyl compounds may also be employed as the heteropoly acid or salt thereof. These uranyl compounds will possess the generic formula:

$$A[UO_2]XO_4 \cdot n\ H_2O$$

in which A is selected from the group consisting of hydrogen, lithium, sodium, potassium, ammonium, copper, magnesium, calcium, barium, strontium, lead, iron, cobalt, nickel, manganese, and aluminum, X is selected from the group consisting of phosphorus and arsenic and n is an integer of from 1 to 4. Some specific examples of these uranyl compounds will include uranyl orthophosphate (HUOP), uranyl orthoarsenate, lithium uranylphosphate, lithium uranylarsenate, sodium uranylphosphate, sodium uranylarsenate, potassium uranylphosphate, potassium uranylarsenate, ammonium uranylphosphate, ammonium uranylarsenate, calcium uranylphosphate, calcium uranylarsenate, barium uranylphosphate, barium uranylarsenate, copper uranylphosphate, copper uranylarsenate, iron uranylphosphate, iron uranylarsenate, cobalt uranylphosphate, cobalt uranylarsenate, nickel uranylphosphate, nickel uranylarsenate, etc.

It is to be understood that the aforementioned listing of organic polymeric compounds, heteropoly acids or salts thereof are only representative of the class of compounds which may be employed in formulating the organic-inorganic blends used in the present invention.

The membranes used in the present invention are prepared by admixing the two components of the blend in a mutually miscible solvent at reaction conditions for a period of time sufficient to form the desired blend. In the preferred membrane, the mutually miscible solvent which is employed to dissolve the components comprises water, although it is contemplated that any other mutually miscible solvent, either inorganic or organic in nature may also be employed. The mixing of the two components of the membrane may be effected at reaction conditions which will include a temperature in the range of from about ambient (20°–25° C.) up to the boiling point of the mutually miscible solvent which, for example, in the case of water is 100° C. The time of reaction which is necessary to form the desired blend will vary with the particular organic polymers and heteropoly acids or salts thereof as well as the solvent and may be within a period of time ranging from about 0.5 up to about 10 hours or more in duration. Upon completion of the reaction period, the blend is cast upon a suitable casting surface which may consist of any suitable material sufficiently smooth in nature so as to provide a surface free of any defects which may cause imperfections on the surface of the membrane. Examples of suitable casting surfaces may include metals such as stainless steel, aluminum, etc., glass, polymer or ceramics. After casting the solution upon the surface, the solvent is then removed by any conventional means including natural evaporation or forced evaporation by the application of elevated temperatures whereby said solvent is evaporated and the desired membrane comprising a thin film of the polymeric blend is formed. In the preferred membrane, the polymeric blend of an organic-inorganic compound will possess a molecular weight ranging from about 2000 up to about 135,000 and preferably greater than 10,000. The thickness of the film can be controlled by the amount of polymer and heteropoly acid or salt thereof which is present in the reaction mixture. In this respect, it is to be noted that the ratio of heteropoly acid or salt and organic polymer may vary over a relatively wide range. For example, the heteropoly acid or salt may be present in the blend in a range of from about 1% to about 70% by weight of the blend while the organic polymer may be present in an amount in the range of from about 99% to about 30% by weight of the blend. Initially, it was believed that the ranges were narrower; about 10% to about 70% for the heteropoly acid on salt and about 90% to about 30% for the organic polymer. The thin film organic-inorganic blend which is prepared according to the process of the present invention will possess a thickness which may range from about 0.1 to about 50 microns and preferably from about 5 to about 20 microns.

The polymer blend membranes may be prepared by placing a predetermined amount of each of the components of the blend, namely, the organic polymer and the heteropoly acid or salt thereof, in an appropriate apparatus such as a flask. After adding the mutually miscible solvent, the mixture is allowed to remain, after thorough admixing thereof, for a predetermined period of time within the range hereinbefore set forth. As an example, poly(vinyl alcohol) and dodecamolybdophosphoric acid may be placed in a flask and dissolved in water which has been heated to 100° C. Upon completion of the desired residence time, the solution is cast upon an appropriate casting surface and the water or other solvent is removed. The desired and resulting polymer blend membrane is then recovered and utilized in an appropriate gas separation apparatus or gas sensor apparatus.

Examples of novel thin film organic-inorganic polymer blends which may be prepared include poly(vinyl alcohol)-dodecamolybdophosphoric acid, poly(vinyl fluoride)-dodecamolybdophosphoric acid, cellulose acetate-dodecamolybdophosphoric acid, polyethylene oxide-dodecamolybdophosphoric acid, polyethylene glycol-dodecamolybdophosphoric acid, poly(vinyl alcohol)-dodecatungstophosphoric acid, poly(vinyl fluoride)-dodecatungstophosphoric acid, cellulose acetate-dodecatungstophosphoric acid, polyethylene oxide-dodecatungstophosphoric acid, polyethylene glycol-dodecatungstophosphoric acid, poly(vinyl alcohol)-dodecamolybdosilicic acid, poly(vinyl fluoride)-dodecamolybdosilicic acid, cellulose acetate-dodecamolybdosilicic acid, polyethylene oxide-dodecamolybdosilicic acid, polyethylene glycol-dodecamolybdosilicic acid, poly(vinyl alcohol)-ammonium molybdophosphate, poly(vinyl fluoride)-ammonium molybdophosphate, cellulose acetate-ammonium molybdophosphate, polyethylene oxide-ammonium molybdophosphate, polyethylene glycol-ammonium molybdophosphate, poly(vinyl alcohol)-uranyl orthophosphate, poly(vinyl fluoride)-uranyl orthophosphate, cellulose acetate-uranyl orthophosphate, polyethylene oxide-uranyl orthophosphate, polyethylene glycol-uranyl orthophosphate, etc. It is to be understood that the aforementioned list of polymer blends is only representative of the class of polymer blend membranes which may be prepared.

It will be helpful in gaining an understanding of the invention to examine initial proof of principle experimentation. Presented first is information on a gas detector which utilizes a reference gas. Following this, information on the use of a solid reference substance in place of reference gas is provided. The information presented in regard to the experimentation is not meant to limit the scope of the invention in any way.

A novel polymer blend membrane was prepared by dissolving poly(vinyl alcohol) and dodecamolybdophosphoric acid in boiling deionized water, the amount of organic polymer and heteropoly acid being sufficient to impart a 50/50 weight percent ratio to the resulting polymer blend membrane. The solution was then poured into an evaporation dish and the water was allowed to evaporate for a period of 16 hours. The resulting blended film was yellow-green in color and possessed a thickness of 20 microns.

Various analyses of the film were performed to determine whether or not the film was in single-phase or two-phase. The blended film was found to be optically transparent, and no phase separation was observed when the film was examined with an optical microscope or SEM. The specimen was also subjected to a glass transition temperature measurement inasmuch as the measurement of the glass transition temperature, or temperatures, of a polymer blend is the most commonly used criteria for determining the number of phases present in a blend. For example, a single-phase organic-inorganic blend will exhibit a single glass transition temperature between the temperatures of the components, while in a two-phase system, two separate temperatures will result. Poly(vinyl alcohol) has a known glass transition temperature of about 71° C., while the melting point temperature of dodecamolybdophosphoric acid is about 84° C. A DSC scan of the film prepared according to the above paragraphs had a peak of 78° C. while no peaks were observed at temperatures corresponding to the glass transition temperatures of poly(vinyl alcohol) or the melting point of dodecamolybdophosphoric acid.

Infrared spectroscopy of the film showed four strong bands appearing at 820 cm$^{-1}$, 885 cm$^{-1}$, 972 cm$^{-1}$, and 1075 cm$^{-1}$. The indication from this analysis is that the bands are associated with intermolecular bonding between the poly(vinyl alcohol) and the dodecamolybdophosphoric acid. In addition to these analyses, it was found that the blended film possessed increased tensile strength and modulus over that which is possessed by either poly(vinyl alcohol) or dodecamolybdophosphoric acid, the increase in tensile strength and modulus perhaps being the result of increased hydrogen bonding due to the formation of a single phase material.

The thin film membrane was cut into a disc having a 1" diameter to form membrane 1 of FIG. 1 and platinum was sputter-deposited onto both sides of the disc. The deposited platinum disc had a thickness ranging from about 100 to about 200 angstroms and a diameter of about 1.2 cm. Deposition was accomplished by means of a Hummer II sputter deposition system supplied by Technics Co. The first few attempts at platinum sputter deposition resulted in degradation of the PVA/DMPA film due to excessive electron bombardment. To reduce the flux of electrons striking the film, the biasing configuration of the sputter deposition system was changed. The addition of a biased screen between the target and film reduced the electron flux to the membrane and permitted metal to be deposited without damage. There are many alternative methods which could have been used to form the platinum deposits, such as thermal evaporation or deposition by means of an ink. The porous structure of sputter deposited catalytic agent is helpful in facilitating spillover of hydrogen ions onto the membrane, but it is not required. Note that hydrogen will migrate through solid platinum.

Referring to FIG. 1, membrane 1 was mounted in test fixture 2, which may also be referred to as a sample cell, membrane housing, or test sensor. The above-mentioned platinum deposits 5 served as catalytic agent to promote dissociation and re-association or combination. Electrical contact was made to the platinum through copper platens 6, which were held in place by springs (not shown) extending between the platens and interior surfaces of the sample cell. Platens 6 did not cover the entire surface of the catalytic agent, though FIG. 1 shows this to be the case. Note that when the catalytic agent is electrically conductive and not discontinuous, electrical contact need be made only at one point. Wire leads 3 and 4 extended from the platens out of the test fixture through means for sealing against gas leakage (not shown). Leads 3 and 4 were connected to EMF and current detection means (not shown). Membrane 1 was sealed into test fixture 2 by O-rings 7 so that there were no gas leakage paths between test gas chamber 8 and reference gas chamber 9. Tubing (not shown) was connected at gas inlets 10 and 11 to provide gas flow into chambers 8 and 9 and was also connected to gas outlets 12 and 13 to conduct gas away from the chambers. Gas cylinders and gas mixing and flow control apparatus (not shown) were used to provide gas to test the sensor of fixture 2 in accordance with the herein described experiments. It must be noted that the gas mixing apparatus was capable of accuracy suitable for proof of principle experimentation but not for more rigorous work. Also, no attempt was made to separately analyze the gas mixtures prepared by diluting purchased gas.

Figure 2:
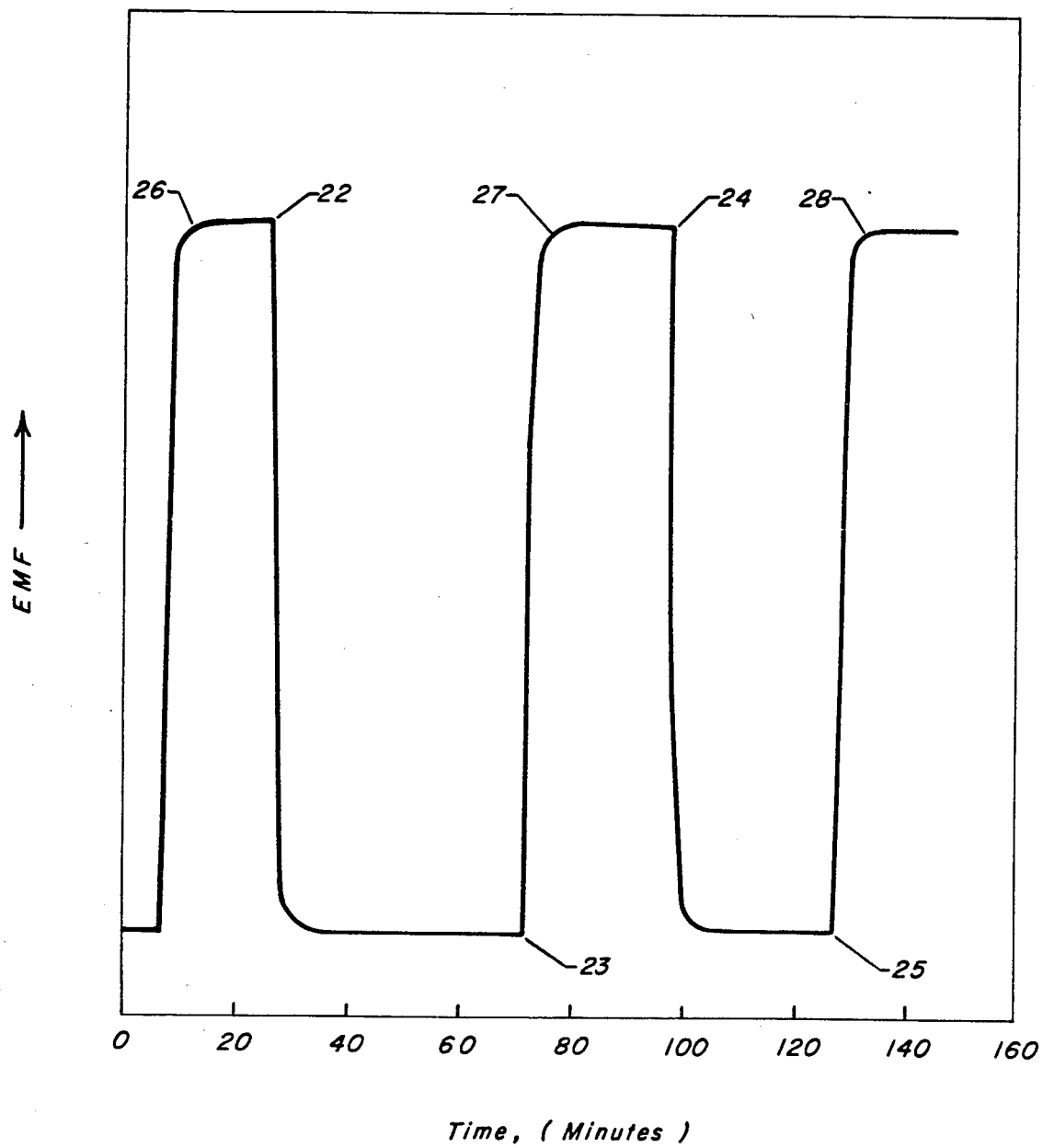
FIG. 2 depicts a portion of the results obtained when gas streams comprising hydrogen were passed through the test sensor shown in FIG. 1. It is a reproduction of the tracing of a strip chart recorder. EMF developed in the test sensor is plotted against time.

Gas flows were established through the chambers of the sample cell with both chamber pressures at essentially one atmosphere, since the chambers were vented directly to atmosphere. One flow was pure hydrogen (hydrogen partial pressure of approximately 1.0 atm.) and the other was a 2% by volume mixture of hydrogen in nitrogen (hydrogen partial pressure of approximately 0.02 atm.). The gas flows were alternated between test gas chamber 8 and reference gas chamber 9 and the voltage across wires 3 and 4 was recorded by means of a standard laboratory strip chart recorder (see FIG. 2). Referring to FIG. 2, the effect of alternating or switching the gas flows can be seen at points 22, 23, 24, and 25. The reproducibility and accuracy was very good. Voltage varied consistently between positive 49.5 millivolts and negative 49.5 mv. Response was Nernstian; the calculated voltage is also 49.5 mv (at a room temperature of 22° C.). Hydrogen flux and current flow were also determined.

Membranes having other amounts of PVA and DMPA were prepared and tested in the same manner as described above for the 50/50 weight percent blend. PVA is commercially available in several nominal molecular weights (MW). Most membranes were prepared with PVA of MW 78,000, though MW 16,000 and 133,000 were also used. Following is a tabulation of data for several membranes with varying blends by weight percent and using a reference to sample gas hydrogen pressure ratio of 100:2. Current (I) is in milliamps. Hydrogen flux is in ft.$^3$/ft.$^2$-hr. times $10^{-3}$.

| PVA/DMPA | I | Flux |
|---|---|---|
| 90/10 | 0.0005 | 0.0056 |
| 75/25 | 0.031 | 0.339 |
| 50/50 | 0.1337 | 1.46 |
| 40/60 | 0.1337 | 1.46 |

The same open-circuit voltage (49.5 mv) was observed for each of the last three blends above. Reproducibility of measurements taken for the 90/10 blend was not good, leading to the conclusion that the maximum amount of PVA usable with DMPA is about 90% by weight. With DMPA contents above about 70% by weight, the membranes were brittle and also appeared to form a two-phase system.

With a PVA/DMPA membrane, it is necessary that some significant amount of water vapor be present in either the sample gas stream or the reference gas stream or both. The amount of water vapor is not critical, as it was in the case of the pressed DMPA wafer, but some is required for the detector to operate properly. In the tests performed, the smallest amount of water vapor used was that needed to cause a relative humidity of about 30% in the gas stream. It is expected that the minimum amount required is at least an order of magnitude less.

In addition to platinum, gold and palladium were deposited on membranes for use as catalytic agent. Nernstian voltage response was observed when palladium was used. Switching gas streams as described above but using a 75/25 membrane with sputter-deposited palladium yielded a strip chart record indistinguishable from that depicted by FIG. 2. Gold electrodes were ineffective; no meaningful voltage response to hydrogen partial pressure was observed. This was not unexpected, as gold, unlike platinum and palladium, does not dissociate molecular hydrogen at room temperature. It is expected that nickel will be effective as catalytic agent if it is desired to utilize the invention at higher temperatures, since nickel is known to dissociate hydrogen at higher temperatures. Other catalytic agents are available and known to those skilled in the art. The catalytic agent need not be electrically conductive; however, then the means for forming electrical connection must be in contact with the catalytic agent over a broad area, to faciliate movement of electrons from sites of the catalytic agent to the electrically conductive substance, or electrode. Areas of membrane which are not adjacent to catalytic agent are not effective in the invention. Hydrogen ions spill over from the catalytic agent to the membrane and then the protons move through the membrane.

Gases other than nitrogen were used to dilute hydrogen passed through the test sensor. Use of helium resulted in no change at all in measured voltages. The presence of small amounts of carbon monoxide (less than 5% by volume) in a 2% hydrogen (by volume) in nitrogen sample gas stream with a 100% hydrogen reference gas stream caused a change in EMF indicative of a large reduction in hydrogen partial pressure. This apparent drop in hydrogen concentration was much larger than the expected drop due to the effect of dilution of sample gas with CO. This is likely due to the competition by CO with molecular hydrogen for adsorption sites on platinum and palladium. The invention cannot be used to measure the amount of hydrogen, or other gas, present in a sample gas which also contains CO, or other substances which interfere in the same manner, unless the amount of CO, or other substance, is known by other means or constant.

In further experimentation, sample gas streams of lower hydrogen partial pressure were passed through the test sensor, the reference gas being pure hydrogen. The membrane used was 75% PVA/25% DMPA with palladium catalyst. Observed EMF (mv) and theoretical EMF (mv), as calculated by the Nernst equation, are as follows for several hydrogen concentrations (expressed in parts per million).

| Concentration | Observed | Theoretical |
|---|---|---|
| 20,000 | 49 | 49 |
| 10,000 | 56 | 58 |
| 2,500 | 77 | 77 |
| 1,000 | 88 | 88 |

It was not possible to check lower concentrations due to limitations of the gas mixing equipment. It is believed that the value of 56 mv, above, is due to a mixture which varied from 10,000 ppm.

Response time of a sensor with a 40% PVA/60% DMPA membrane having platinum catalyst was tested. When the 100% and 2% gas streams were switched between chambers as described above, the time required for the voltage to change from 10% to 90% of its final value was approximately 6 seconds. This can be illustrated by reference to FIG. 2 and the near vertical portion of the curve at about 25 minutes and starting at point 22. The time required to trace about 80% of the length of a similar curve was about 6 seconds. It should be noted that the sample cell used is not necessarily designed for quick response.

The above description has dealt with hydrogen detection. It is obvious that any substance capable of dissociating in the presence of a catalyst to yield hydrogen ions may be detected in the same manner. An example is hydrogen chloride. The Nernst equation applies in a manner similar to that described below. The methods and apparatus described herein are also useful in detecting any gaseous component of a gas sample which is capable of combining with hydrogen ions. Oxygen may be used to illustrate this embodiment. Protons passing through the membrane from a reference chamber will combine with oxygen in a sample gas and electrons from the external circuit (for example, wires 3 and 4 of FIG. 1) to form water, in contrast to the hydrogen detector, wherein hydrogen is formed. The Nernst equation is applicable; the $E_o$ term is not 0, as it is when the same substance is present on both sides of the membrane, and the partial pressure of oxygen to the one-half power times the partial pressure of hydrogen divided into the partial pressure of water replaces the analogous term of the equation. Hydrocarbons capable of hydrogenation or dehydrogenation may be subjects of detection. Examples are cyclopentadiene, benzene, isoprene, cyclohexane, and isoamylene.

Membranes of PVA and uranyl orthophosphate (HUOP) were made and tested in the apparatus of FIG. 1 after platinum was sputter-deposited on them. In every case, the blend was prepared with equal weights of PVA and HUOP (before further treatment). PVA of three different molecular weights was used. PVA and HUOP were mixed with water and cast in the same manner as described above. Since HUOP is slightly soluble in water, large amounts of HUOP remained undissolved in the solutions prepared. Before casting, some solutions were filtered through Sargent-Welch S-32915-D filter paper, some were filtered through a 0.22 micron (nominal rating) Millipore filter, and those of one PVA molecular weight only (16,000) were ultracentrifuged for 30 minutes. In most cases, the membranes exhibited Nernstian behavior. The following table summarizes the results for the various membranes, including those cast without filtering or ultracentrifuging. N denotes Nernstian response and non-N denotes non-Nernstian response. A dash denotes that the combination was not tested.

| Treatment | Molecular Weight | | |
|---|---|---|---|
| | 16,000 | 78,000 | 133,000 |
| None | Non-N | N | Non-N |
| S-W Filter | N | N | Non-N |
| Millipore | N | N | N |
| Centrifuge | N | — | — |

The following information was developed using only membranes cast with PVA/HUOP solutions after passage through the Millipore filter and a reference gas of pure hydrogen flowing through reference gas chamber 9 of sample cell 2 (FIG. 1). Using a membrane comprising PVA of 16,000 MW and switching the sample gas between 100% hydrogen and 20% hydrogen, an EMF curve similar to FIG. 2 resulted. The voltage varied between 0 and −18.5 mv instead of the −20.5 mv predicted by the Nernst equation. With a 78,000 MW PVA membrane and a 0.1% hydrogen stream, there was a difference of 0.2 mv between the recorded EMF and the theoretical of −87.8 mv. With a 133,000 MW PVA membrane and a 20% hydrogen stream, there was a difference of 0.2 mv between the recorded EMF and the theoretical of −20.5 mv. In each of these three cases, it appears that the response time is faster when the sample gas concentration is switched to 100% hydrogen than when it is switched to the lower hydrogen concentration. This is apparent from the strip chart recorder tracing (not shown herein) because there are square corners at the 0 voltage line and completely horizontal lines traced at 0 voltage, in contrast to the rounded approach to the lower EMF values. This could be shown on FIG. 2 by making square corners at points 26, 27, and 28. The cause of this behavior has not yet been determined. A 78,000 MW PVA membrane was used in taking EMF readings with sample gases of concentrations from 100% hydrogen to approximately 300 ppm hydrogen. A plot of EMF versus ln(hydrogen concentration) yielded a straight line with a slight curve at the low concentration end. We are convinced that the sensor response is linear and the deviation shown by the curve was due to equipment limitations at low concentrations. A sensor was tested continuously for 96 hours, with the sample gas being switched from 100% to 0.1% hydrogen and vice versa every 20 minutes. The strip chart recorder tracing for the first hour was the same as that for the last hour. There was no drift of baseline, change in EMF, or change in response time. In all of the experimentation with PVA/HUOP membranes, no water vapor was added to either the reference gas or the sample gas. The purchased gas, before dilution, contained a maximum of 20 ppm water. It can thus be concluded that the presence of water vapor is not required with this particular blend, as it is when using a PVA/DMPA blend in a sensor, or sample cell.

As mentioned above, large quantities of HUOP remained undissolved, leading to a brief investigation of the amount of HUOP in the membrane. The results were that membranes containing as little as 1% by weight HUOP were prepared.

Figure 3:
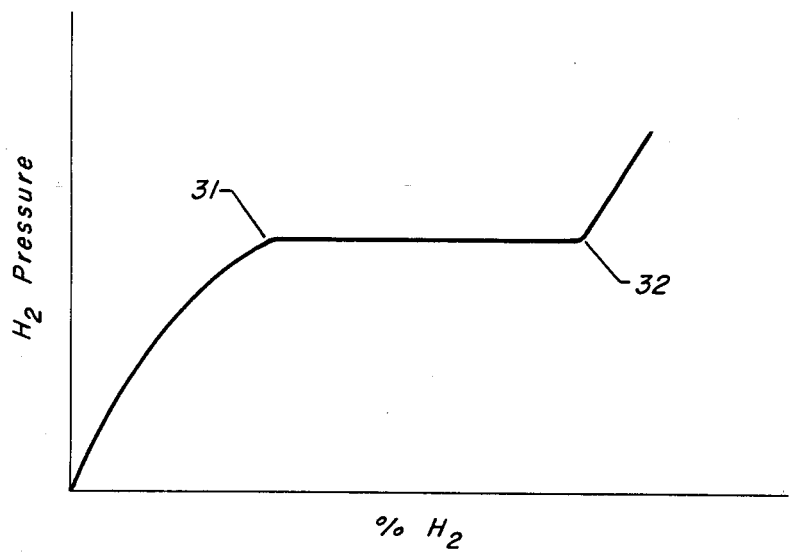
FIG. 3 is a portion of a phase diagram of a solid reference substance capable of use in the present invention, in which hydrogen partial pressure of the substance is plotted against the amount of hydrogen in the substance. If the plot were extended to larger amounts of hydrogen, several plateaus might appear.

It is highly desirable to avoid the use of a reference gas in the methods and apparatus of detection described herein. This may be accomplished by using a reference substance in the form of a solid. As discussed herein, it is necessary that a media with a known partial pressure of hydrogen be used as a reference. It is also necessary that the reference partial pressure remain substantially constant as hydrogen is added to or removed from the reference substance. In the sensor of the present invention, the EMF developed is an open circuit value. Thus, theoretically there are no electrons flowing in the external circuit to combine with protons passing through the membrane and therefore no change in reference hydrogen concentration. Of course, in actuality there is a small current flowing and reference hydrogen concentration is constantly changing. A reference media must possess the characteristic of constant hydrogen partial pressure while hydrogen concentration changes. FIG. 3 depicts a portion of a phase diagram of a solid substance suitable for use as a reference substance in the present invention. For a sensor having a solid reference substance to function properly, the hydrogen concentration must lie on the plateau, or horizontal portion, of the curve of FIG. 3, the plateau lying between points 31 and 32. As the hydrogen content of the reference substance increases or decreases due to operation of the sensor, that is, as hydrogen, or other substance, forms from the protons which pass through the membrane and the electrons which flow in the external circuit, the point representing the reference substance moves along the plateau However, as long as the point is on the plateau the hydrogen partial pressure remains constant and, therefore, the reference substance is useful. It can be seen that a particular reference substance has a limited life. Since the time required to change the hydrogen concentration beyond the limits represented by points 31 and 32 can easily be measured in months or years, the use of a solid reference is practical. Since the flow of protons through the membrane may be in either direction, hydrogen content of the solid reference substance may increase or decrease. When it passes above point 32 or below point 31, the reference substance must be replaced.

Metal hydrides are, in general, suitable for use as solid reference substances in this invention, since their phase diagrams are usually similar to that of FIG. 3. There may be several plateaus on one diagram, so that there is a choice of reference partial pressures while using one particular substance. Examples of metal hydrides include substances consisting of hydrogen and oxygen with tungsten, molybdenum, vanadium, or iridium, hydrogen-zirconium-nickel compounds, hydrogen-zirconium-platinum compounds, and compounds of hydrogen with platinum and/or palladium. Further examples comprise compounds of hydrogen and elements of atomic numbers of 3, 11, 12, 19 through 28, 37 through 48, 55 through 60, 62, 64, 72 through 78, 90, and 92.

Figure 4:
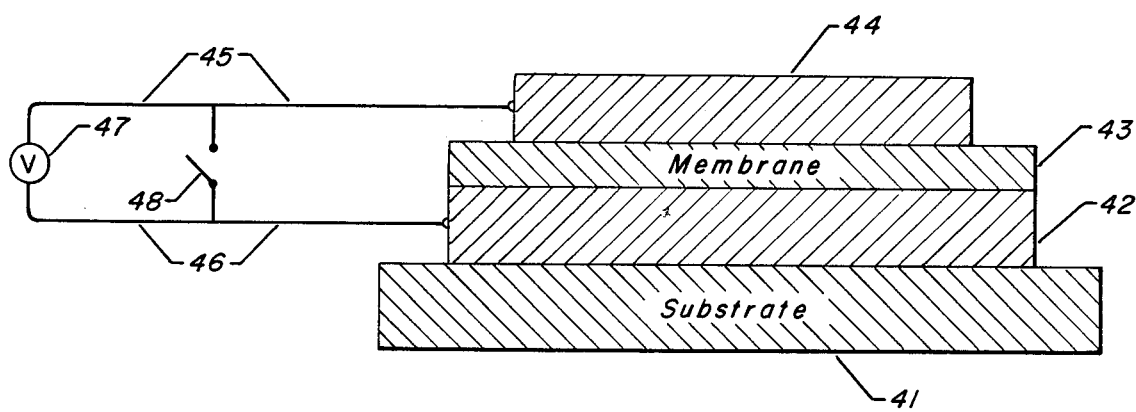
FIG. 4 is a schematic representation, in cross-section, of the test sensor used in initial proof of principle experimentation for this invention. It is not to scale.

In proof of principle experimentation, the apparatus of FIG. 4 was fabricated. Palladium layer 42 of approximately 5000 angstroms thickness was sputter-deposited on substrate 41. The substrate used was silicon, since it was at hand and possessed an appropriate surface. Choices of substrate may be made from a wide variety of materials and are not a part of the invention. The palladium layer was moistened with DI water and 50/50 PVA/DMPA membrane 43 was cast over it in the same manner as described above. The membrane had a thickness of approximately 40 microns. Platinum layer 44 was sputter-deposited on membrane 43 to a thickness of approximately 200 angstroms. Wires 45 and 46 were attached to platinum layer 44 and palladium layer 42 as shown in FIG. 2. The wires were connected to voltmeter 47. In addition, switch 48 was provided in parallel with the voltmeter to complete an external circuit. The apparatus was exposed to hydrogen gas for two days, with switch 48 closed, to add hydrogen to palladium layer 42 to provide the reference substance. Hydrogen dissociated at platinum layer 44 and the protons passed through membrane 43 while the electrons from the dissociated molecules flowed through the external circuit consisting of wires 45 and 46 and switch 48. It is not necessary to form the reference substance in place in this manner; palladium hydride could have been deposited on the substrate. The palladium hydride served as both catalyst agent and reference substance.

After completion of fabrication of the sensor, hydrogen gas at various concentrations was passed over the sensor. This was accomplished by passing gas through tubing inserted under the lip of an upside-down beaker placed over the sensor while it was resting on a lab bench. EMF obtained (from voltmeter 47) at each partial pressure of hydrogen is as follows:

| mv | atm. |
|---|---|
| 250 | 0.59 |
| 310 | 0.50 |
| 360 | 0.39 |
| 400 | 0.355 |
| 460 | 0.225 |

When these values are plotted on a semi-logarithmic scale, they do not fall exactly on the straight line which represents the theoretical values of EMF versus partial pressure, but fall closely on either side of the line. This lack of exact agreement is felt to result from the relatively crude gas mixing equipment and experimental procedures and it is expected that better agreement with the theoretical would result from more sophisticated experimentation. Further, as mentioned herein, exact agreement is not required of a commercial sensor.

The reference partial pressure of hydrogen which is used in the Nernst equation to determine EMF is easily calculated. For example, niobium hydride has a hydrogen partial pressure of approximately $10^{-6}$ atmospheres, as calculated by the relationship $$\ln P = \frac{H}{RT} - \frac{S}{R},$$

where H=enthalpy of formation, S=entropy, P=$P_2$ or $P_1$ as defined above, and R and T are as defined above. Experiments with niobium hydride were done.

As is common in many analysis instruments, the sample gas provided to a sensor may require conditioning in order to achieve effective detection. Of course, any particulate matter and liquid droplets are removed. The extent of conditioning depends on the particular gas involved and its state. For example, an extremely hot gas must be cooled to a sufficiently low temperature so as not to degrade the apparatus by melting sensor components, including the membrane. A relatively cold gas may need to be heated to a temperature which promotes a reasonable response time of the appparatus. A related factor to be considered is the necessity for knowing the temperature for use in the Nernst equation. This temperature may be measured or the temperature may be maintained at a pre-established constant value. If the calibration gas temperature is maintained at the same value, the matter is simplified. Water vapor and/or other substances are often removed from or added to a sample gas stream. Other sample-conditioning techniques may be required. For example, in a situation where the concentration of the unknown substance is extremely large and capable of saturating the apparatus, the sample may be diluted by addition of a known amount of inert gas. The actual concentration of undiluted sample can then easily be calculated.

A detector may take many forms. A portable battery-operated unit may be used as a "sniffer" to detect the presence in the atmosphere of a particular gas due to leakage from a closed system. A detector may be permanently mounted in a particular location to detect leaks. When conditioning is not required, a detector may be fabricated for insertion directly into a process pipeline. When a gas sample must be conditioned, a small sidestream may be withdrawn from a process pipeline on a continuous or intermittent basis and passed through a sample gas chamber.

As used herein, the term "detection" includes not only sensing presence or absence of the detected substance, but measurement of the amount of substance present, either in order of magnitude or exact amounts. Gas sample refers to any portion of a gas which is the subject of detection. A gas sample may have only one component. Sample cell or membrane housing or test fixture refers to a housing or fixture which holds an electrolyte element and other required components. FIG. 4 depicts a membrane housing. Sensor is a general term denoting sensing apparatus, such apparatus comprising a membrane housing. Membrane or electrolyte element refers to an ion conducting substance suitable for use as an electrolyte in the concentration cell of this invention which has been formed into a particular physical entity, either with or without additional substances, for use in the invention. Where an electrolyte element surface is referred to as in common with a gas or gas chamber, the meaning is the same as exposed to a gas or gas chamber and such reference does not preclude the presence of catalytic agent and electrodes at or covering the surface. Gas may diffuse through covering material. Sample gas chamber refers to any space in which gas which is the subject of detection exists. For example, a sample cell can form a part of a pipeline wall such that the gas flowing in the pipeline is the sample gas and the pipeline is the sample gas chamber. The term "gas" is used herein to include vaporized liquids regardless of boiling point characteristics of the substance. As used herein, miscible means capable of being mixed where there may only be a very small degree of solubility.

The design of sample cells, or detectors, or membrane housings, is well known. Many configurations are possible; FIG. 1 provides an example of one type. Another type may be visualized as constructed from a standard pipe plug of 3 or 4 inch size. The plug is hollowed out to provide a cavity to serve as a reference chamber. The membrane is placed at the location of the former inner surface of the plug and retained in place and sealed by appropriate means. The plug is screwed into a pipeline, the pipeline serving as sample gas chamber. Passages are drilled to the cavity from the outside surface of the plug to serve as reference gas inlet and outlet if a solid reference is not used. If a greater membrane surface area is desired, a detector may be fabricated in the form of a cylindrical probe for insertion into a pipeline. Membrane material may be placed over a perforated pipe which is sealed at one end. The interior of the pipe is the reference gas chamber. It may be desirable to protect the membrane and catalytic agent by covering it with a porous substance through which sample gas can pass.

The apparatus depicted in FIG. 4 is an example of a sample cell or membrane housing. The space adjacent to catalytic agent 44 comprises the sample gas chamber. The space occupied by reference substance 42 comprises the reference chamber. Membrane 43 comprises a substantially imporous partition separating the chambers. If it were desired to use a catalytic agent separate from the reference substance, catalytic agent would be depicted as a layer between the layers 42 and 43.

We claim as our invention:

1. An apparatus for detection, in a gas sample, of a gaseous component, which is capable, in the presence of a catalytic agent, of dissociating to yield hydrogen ions or of combining with hydrogen ions, which apparatus comprises:

(a) a thin film organic-inorganic membrane which comprises a blend of: (1) from about 10% to about 70% by weight of a heteropoly acid and salts thereof having the generic formula:

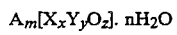
    $A_m[X_xY_yO_z] \cdot nH_2O$ in which X is selected from the group consisting of boron, aluminum, gallium, silicon, germanium, tin, phosphorus, arsenic, antimony, bismuth, selenium, tellurium, iodine, and metals of the first, second, third and fourth transitional metal series of the Periodic Table and where Y is dissimilar from X and is selected from at least one metal of the first, second, third and fourth transitional metal series of the Periodic Table, A is selected from the group consisting of hydrogen, ammonium, sodium, potassium, lithium, rubidium, cesium, beryllium, magnesium, calcium, strontium and barium, m is an integer of from about 1 to 10, y is a integer of from 6 to 12 based on x being equal to 1, z is an integer of from 30 to 80 and n is an integer of from 3 to 100 and, (2) from about 90% to about 30% by weight of a polymer compatible with said compound selected from the group consisting of poly (vinyl alcohol), poly (vinyl fluoride), polyethylene oxide, polyethyleneimine, polyacrylic acid, polyethylene glycol, cellulose acetate, polyvinylmethylethyl ether and phenol formaldehyde resins;

(b) an organic-inorganic membrane housing comprising a sample gas chamber and a reference chamber separated by a substantially imporous partition comprising said organic-inorganic membrane, said membrane having a first surface in common with the sample gas chamber and a second surface in common with the reference chamber;

(c) two separate portions of catalytic agent effective to promote dissociation and combination, a first portion in contact with said first surface and a second portion in contact with said second surface of said membrane;

(d) a reference substance in said reference chamber and in contact with said second catalytic agent portion, which substance exhibits a substantially constant known hydrogen partial pressure during use of said detection apparatus; and, (e) means for forming electrical connection in operative contact with said first portion of catalytic agent at said first surface and with said second portion of catalytic agent at said second surface.

2. The apparatus of claim 1 further characterized in that said catalytic agent is selected from a group consisting of platinum, nickel, palladium, and alloys thereof.

3. The apparatus of claim 1 further characterized in that said catalytic agent is electrically conductive.

4. The apparatus of claim 1 further characterized in that said catalytic agent is porous to said gaseous component.

5. The apparatus of claim 1 further including means to adjust the operating temperature of said membrane housing.

6. The apparatus of claim 1 further including means to supply sample gas to the sample gas chamber.

7. The apparatus of claim 1 further including means to measure EMF connected between said means for forming electrical connection.

8. The apparatus of claim 7 further including means to convert said EMF measurement to concentration.

9. The apparatus of claim 1 in which said membrane possesses a thickness of from about 0.1 to about 50 microns.

10. The apparatus of claim 1 in which said polymer comprises poly(vinyl alcohol) and said heteropoly acid comprises dodecamolybdophosphoric acid.

11. The apparatus of claim 1 further characterized in that said reference substance is a metal hydride.

12. The apparatus of claim 1 further characterized in that a single substance serves as both reference substance and catalytic agent.

13. The apparatus of claim 1 further characterized in that said reference substance and catalytic agent is palladium hydride.

14. A method of detecting, in a gas sample, a gaseous component capable, in the presence of a catalytic agent, of dissociating to yield hydrogen ions or of combining with hydrogen ions, said method comprises:
(a) contacting said gas sample with a first surface of an imporous thin film organic-inorganic membrane comprising a blend of: (1) from about 10% to about 70% by weight of a heteropoly acid and salts thereof having the generic formula:

$$A_m[X_xY_yO_z] \cdot nH_2O$$

in which X is selected from the group consisting of boron, aluminum, gallium, silicon, germanium, tin, phosphorus, arsenic, antimony, bismuth, selenium, tellurium, iodine, and metals of the first, second, third and fourth transitional metal series of the Periodic Table and where Y is dissimilar from X and is selected from at least one metal of the first, second, third and fourth transitional metal series of the Periodic Table, A is selected from the group consisting of hydrogen, ammonium, sodium, potassium, lithium, rubidium, cesium, beryllium, magnesium, calcium, strontium and barium, m is an integer of from about 1 to 10, y is an integer of from 6 to 12 based on x being equal to 1, z is an integer of from 30 to 80 and n is an integer of from 3 to 100 and, (2) from about 90% to about 30% by weight of a polymer compatible with said compound selected from the group consisting of poly (vinyl alcohol), poly (vinyl fluoride), polyethylene oxide, polyethyleneimine, polyacrylic acid, polyethylene glycol, cellulose acetate, polyvinylmethyethyl ether and phenol formaldehyde resins having a first portion of catalytic agent in contact therewith effective to promote dissociation and combination;
(b) contacting a reference substance which exhibits a substantially constant known hydrogen partial pressure, with a second surface of said organic-inorganic membrane of step (a) having a second portion of catalyst in contact therewith; and,
(c) detecting EMF between means for forming electrical connection in operative contact with said first portion of catalytic agent at said first surface and with said second portion of catalytic agent at said second surface of said membrane.

15. The method of claim 14 further characterized in that said gaseous component is elemental hydrogen.

16. The method of claim 14 further characterized in that said gaseous component is elemental oxygen.

17. The method of claim 14 further characterized in that water is added to said gas sample before the gas contacts said membrane.

18. The method of claim 14 further characterized in that the concentration of said gaseous component in the sample is adjusted before the sample contacts said membrane.

19. The method of claim 14 further characterized in that the temperature of said gas sample is adjusted before said gas contacts said membrane.

* * * * *